US009040934B2

(12) United States Patent
Baroni et al.

(10) Patent No.: US 9,040,934 B2
(45) Date of Patent: May 26, 2015

(54) TWO-DIMENSIONAL DETECTION SYSTEM FOR NEUTRON RADIATION IN THE FIELD OF NEUTRON SCATTERING SPECTROMETRY

(71) Applicants: Centre National De La Recherche Scientifique (CNRS), Paris (FR); Commissariat A L'Energie Atomique, Paris (FR)

(72) Inventors: Patrick Francois Baroni, Les Ulis (FR); Laurence Marie Noirez, Orsay (FR)

(73) Assignees: CENTRE NATIONAL DE LA RECHERCHE SCIENTIFIQUE (CRNS), Paris (FR); COMMISSARIAT A L'ENERGIE ATOMIQUE, Paris (FR)

( * ) Notice: Subject to any disclaimer, the term of this patent is extended or adjusted under 35 U.S.C. 154(b) by 0 days.

(21) Appl. No.: 14/262,914

(22) Filed: Apr. 28, 2014

(65) Prior Publication Data
US 2014/0231661 A1    Aug. 21, 2014

Related U.S. Application Data

(63) Continuation of application No. 11/908,096, filed on Sep. 7, 2007, now abandoned.

(30) Foreign Application Priority Data

Mar. 10, 2005  (FR) ..................................... 05 02379
Mar. 9, 2006   (WO) ................. PCT/EP2006/060611

(51) Int. Cl.
G01T 3/06      (2006.01)
G01N 23/207    (2006.01)
G01T 3/00      (2006.01)

(52) U.S. Cl.
CPC .............. *G01T 3/06* (2013.01); *G01N 23/2073* (2013.01); *G01T 3/00* (2013.01); *G01T 3/001* (2013.01); *G01T 3/065* (2013.01)

(58) Field of Classification Search
CPC ......................................................... G01T 3/06
USPC ................................................... 250/390.11
See application file for complete search history.

(56) References Cited

U.S. PATENT DOCUMENTS 3,979,594 A   9/1976  Anger
4,587,555 A   5/1986  Carollo et al.
(Continued)

FOREIGN PATENT DOCUMENTS

EP    1469303 A1   10/2004
JP    2000180997    6/2000
(Continued)

OTHER PUBLICATIONS

B. Schillinger, "Neutron detectors using CCD cameras," in Proc. Int. Workshop on Position-sensitive neutron detectors, Berlin, Germany, Jun. 28-30, 2001.
(Continued)

*Primary Examiner* — David Porta
*Assistant Examiner* — Mindy Vu
(74) *Attorney, Agent, or Firm* — Miles and Stockbridge

(57) ABSTRACT

This invention relates to a two-dimensional detection system for neutron radiation comprising a means (1) for emitting a neutron beam (10), a support means (2) adapted for receiving a sample (3), a photoemission means (5) adapted for being activated by a neutron radiation, a cooled low light level charge-coupled detection device (7). The emission means (1) emits a monochromatic neutron beam (10). The system further comprises a filter means (4), the filter means (4) being located between the support means (2) and the photoemission means (5) and being adapted for trapping at least a substantial part of the monochromatic neutron beam transmitted (12) by the sample (3), and an amplification means (6) located upstream the charge-coupled detection device (7) and coupled with the charge-coupled detection device (7).

32 Claims, 6 Drawing Sheets

(56) References Cited

U.S. PATENT DOCUMENTS

| | | | |
|---|---|---|---|
| 6,011,266 | A | 1/2000 | Bell |
| 6,184,531 | B1 | 2/2001 | Smart et al. |
| 7,244,947 | B2 | 7/2007 | Polichar et al. |
| 2004/0206908 | A1 | 10/2004 | Lange et al. |
| 2005/0017181 | A1 | 1/2005 | Kearfott et al. |
| 2005/0037224 | A1 | 2/2005 | Orford et al. |
| 2005/0119868 | A1* | 6/2005 | Scheidemann et al. ........ 702/196 |
| 2006/0083350 | A1* | 4/2006 | Gerndt et al. ................... 378/70 |
| 2007/0007464 | A1 | 1/2007 | Lange et al. |
| 2007/0253520 | A1 | 11/2007 | Sim et al. |
| 2008/0298551 | A1 | 12/2008 | Ando |

FOREIGN PATENT DOCUMENTS

| | | |
|---|---|---|
| JP | 2000180997 A | 6/2000 |
| JP | 2003083916 | 3/2003 |
| JP | 2003083916 A | 3/2003 |
| JP | 2003239617 | 11/2003 |
| JP | 2003329617 A | 11/2003 |
| WO | 2004081551 A1 | 9/2004 |

OTHER PUBLICATIONS

Kohlbrecher et al., "The new SANS instrument at the Swiss spallation source SINQ", Journal of Applied Crystallography Munksgaard International Booksellers & Publishers Denmark, vol. 33, No. 1, Jun. 2000, pp. 804-806.

Database Inspec [Online] the Institution of Electrical Engineers, Stevenage, GB; Fakirov S: "Beam stop with variable diameter for small angle scattering" XP002290241, Database accession No. 2503432, abstract & Bulgarian Journal of Physics, Bulgaria, vol. 12, No. 2, 1985, pp. 173-177, ISSN: 03239217.

Del Mar Ventures, 4119 Twilight Ridge, San Diego, CA 92130: "Position-Sensitive (Imaging) Detector of Neutron" [Online], Mar. 17, 2004, pp. 1-2.

Ottonello P. et al, "Slow neutron imaging using scintillating glass optical fibers" Meuclear Instruments & Methods in Phyiscs Research, Section A (Accelerators, Spectrometers, Detectors and Associated Equipment) Netherlands, vol. 349, No. 2-3, Oct. 1, 1994, pp. 526-531.

Pleinert H et al: "Design of a new CCD-camera neutron radiography detector" Nueclear Instruments & Methods in Phyiscs Research, Section-A: Equipment, Slsevier, Amsterdam, NL, vol. 399, No. 2-3, Nov. 11, 1997, pp. 382-390.

Databse WPI, Section Ch., Week 2003 57, Derwent Publications Ltd., London, GB; Class J04, AN 2003-599246, XP002352049 & CN 1 421 690 A (Shanghai Precision Optical Instr Inst), Jun. 4, 2003, abstract.

International Search Report, PCT/EP2006060611, dated Nov. 7, 2006.

Japanese Office Action dated Jan. 4, 2012, issued in counterpart Japanese Application No. 2008-500205.

\* cited by examiner

FIG_7
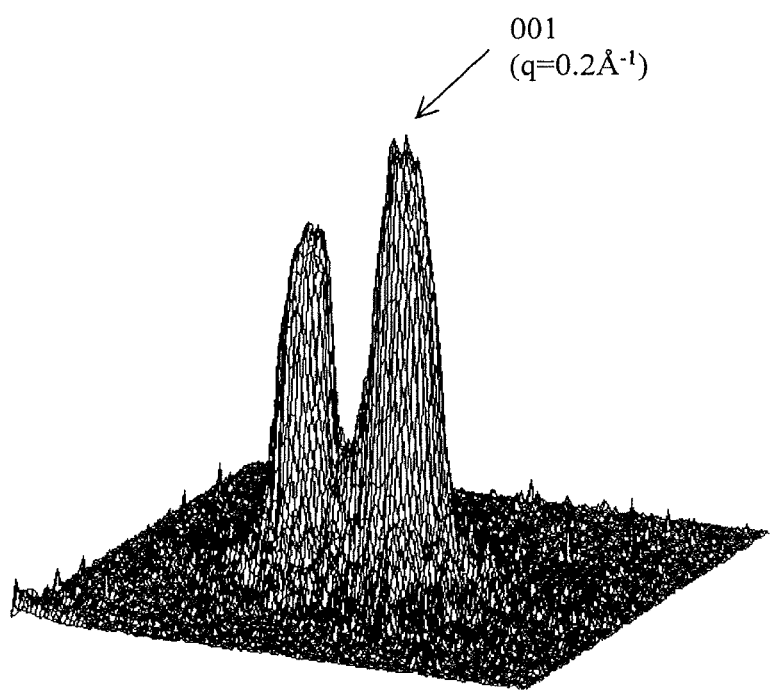

TWO-DIMENSIONAL DETECTION SYSTEM FOR NEUTRON RADIATION IN THE FIELD OF NEUTRON SCATTERING SPECTROMETRY

CROSS REFERENCE TO RELATED APPLICATIONS

This application is a continuation of U.S. application Ser. No. 11/908,096, filed Jul. 7, 2007, which is a §371 National Stage Application of PCT/EP2006/060611, filed Mar. 9, 2006, which claims priority to French Application No. 0502379, filed Mar. 10, 2005, each of these applications are hereby incorporated by reference in their entirety.

FIELD OF THE INVENTION

This invention relates to the field of spectrometry and particularly the neutron scattering spectrometry.

TECHNICAL BACKGROUND

Neutron scattering is a very powerful technique complementary to X-ray scattering for the study of the matter organisation. The neutron scattering techniques provide a powerful means of characterising the structural organisation at the scale of a few Angstroms (Å) up to a few hundred and even a few thousand Angstroms. Unlike X-ray scattering in which the X-radiation interacts with the electronic cloud of atoms, neutrons interact with the atomic nuclei of the sample. The resulting scattering is specific to each isotope, very different particularly for the hydrogen and the deuterium, so that an isotopic contrast can be created in organic materials. Furthermore, unlike X-rays techniques, the neutron scattering technique is a non-destructive method and presents a much higher penetration length than the X-radiation.

The neutron scattering technique associated with two-dimensional position sensitive image integrating detectors enables two-dimensional observation of the scattering space.

A first group of detectors is composed of gas detectors combined with wire chambers (see R. Allemand, J. Bourdel, E. Roudaut, P. Convert, K. Ideb, J. Jacobe, J. P. Cotton, B. Farnoux, "Nucl. Instr. Meth.", 126, 29 [1975]; Y. Giomataris, Ph. Rebourgeard, J. P. Robert, G. Charpak, "NIM" A376 [1996] 29; C. Petrillo et al., "Nucl. Instr. and Meth" A378 [1996] 541 & A424 [1999] 523; G. Brickner et al, "Nucl. Instr. and Meth" A392 [1997] 68). This detection category is usually devoted to the study of neutron scattering phenomena at small angles. These spectrometers have a low spectral resolution.

A second group of two-dimensional detection instruments is composed of devices of the Image Plate type (C. Wilkinson et al, "Neutrons, X-Rays and Gamma Rays" 1737[1992] 329) that comprise a scintillator coupled with a laser. This principle comprises 3 steps; the first consists in charging the scintillating plate, the second in reading the plate using a laser for revealing the number of charges, and finally the incrementation managed by computer. This technique is widely used for X-rays diffusion and is still very difficult to be adapted for the neutrons use.

Observation at wide angles is usually carried out by scanning the reciprocal space along a single direction rather than two directions simultaneously; this is the case for linear multi-counters or 2 or 3-axis elastic diffusion spectrometers.

Nevertheless, two-dimensional observation at wide angles is important for the study of the local organisation, and particularly in the case of structured materials and/or fluids subjected to the action of anisotropic stresses such as pressure gradients, fluid flow, etc.

Neutronography usually consists in using an incident polychromatic neutron beam placed on the trajectory of a sample, to reveal a picture of the transmission/absorbing properties through the sample.

A detector in the neutronography domain has been proposed (see S. Koemer, E. Lehmann, P. Vontobel, "Nucl. Inst. and Meth." A454 [2000] 158-164) that uses a scintillator sensitive to neutrons coupled to a charge-coupled detector. Nevertheless, this detector is not adapted to a quantitative measurement of the signal, and is not enough sensitive for a quantitative characterisation of the organisation of a material at molecular or atomic scale.

It is therefore a goal of the invention to provide a two-dimensional detection system for neutron radiation that enables a quantitative detection of the number of neutrons scattered by a sample, particularly at wide diffusion angles, and that further overcomes at least one of the above-mentioned disadvantages.

SUMMARY OF THE INVENTION

To this end is provided, according to the invention, a two-dimensional detection system for neutron radiation as defined below in the claims.

More precisely, there is provided a two-dimensional detection system for neutron radiation comprising a means for emitting a neutron beam, a support means adapted for receiving a sample, a photoemission means adapted for being activated by a neutron radiation, a cooled low light level charge-coupled detection device, characterised in that the emission means emits a monochromatic neutron beam and in that the system further comprises a filter means, the filter means being located between the support means and the photoemission means and being adapted for trapping at least a substantial part of the monochromatic neutron beam transmitted by the sample, and an amplification means located upstream the charge-coupled detection device and coupled with the charge-coupled detection device.

Preferred but non-limitative aspects of the two-dimensional detection system for neutron radiation according to the invention are as follows:
- the filter means traps the entire monochromatic neutron beam transmitted by the sample;
- the photoemission means emits alpha radiation originating from a single nuclear reaction. It may be for example a lithium-based scintillator, such as a composite material based on lithium sulphide or on lithium fluoride;
- the photoemission means is in the form of a plate with a length of between 5 and 100 cm, a width of between 5 and 100 cm and a thickness of less than or equal to 1.2 mm. This plate may be plane or curved;
- the photoemission means is lined with a surface opaque to light and transparent to neutron radiation, and located on the inlet of the photoemission means. This opaque surface may be formed from a rigid material, in aluminium for example, and adapted for holding the photoemission means in place;
- the charge-coupled detection device enables coding on at least 12 bits, and preferably on 16 bits;
- the charge-coupled detection device is a camera adapted for variable pause times;
- the photoemission means, the amplification means and the charge-coupled detection device are enclosed in a box designed such that no light radiation other than that emitted by the photoemission means can penetrate inside. The photoemission means and the charge-coupled detection device coupled with the amplification means respectively form the inlet end and outlet end of the box;

the system further comprises a protection means capable of reducing the influence of parasite radiation between support means for the sample and the photoemission means. This protection means may be a conical or pyramid shaped element, having the photoemission means as its base and being located between the support means for the sample and the photoemission means. It may also be a casing comprising a cylindrical part and a tapered end part, and surrounding the box;

the protection means includes sidewalls adapted for absorbing parasite radiation not originating from the sample;

the protection means contains an inert gas or a primary vacuum, wherein the inert gas is helium, argon or nitrogen;

the box comprises inside walls adapted for absorbing neutron and gamma radiation;

the system further comprises a mirror, that may be plane or curved, adapted for reflecting only light radiation emitted by the photoemission means towards the amplification means. This mirror may be made from aluminised quartz and is less than or equal to 10 mm thick.

the system further comprises a means for absorbing neutron and gamma radiation, this absorption means being arranged at the outlet of the photoemission means;

the amplification means and the charge-coupled detection device are surrounded by a shield for stopping gamma radiation. This shield is a metal with a thickness and a density such that the product of the thickness and the density is greater than or equal to 34. One could for example use a 2 cm thick shield of tungsten.

the system further comprises a collimation device arranged between the emission means and the support means, and outputting an output neutron beam with a diameter of between 0.5 and 15 mm.

This invention also relates to a two-dimensional detection method for neutron radiation comprising the steps consisting of emitting a neutron beam towards a sample, transforming the neutron beam output from the sample into photons, detecting the photons emitted by a cooled low light level charge transfer detection device, the method being characterised in that it further comprises the steps consisting of transforming the neutron beam emitted towards the sample into a monochromatic neutron beam, filtering the neutron beam output from the sample so as to trap at least a substantial part of the monochromatic neutron beam transmitted by the sample, amplifying the photon radiation upstream the cooled low light level charge transfer detection device.

BRIEF DESCRIPTION OF THE DRAWINGS

Other special features and advantages of the invention will become clear from the following description which is purely illustrative and not limitative, and should be read with reference to the appended figures, wherein:

FIG. 7 is a three-dimensional observation of order 001 of a Bragg reflection on an oriented layered liquid crystal measured at small angles using the detection system according to the invention.

DETAILED DESCRIPTION OF THE DRAWINGS

The two-dimensional detection system for neutron radiation will now be described with reference to FIGS. 1, 2 and 3. Equivalent elements shown in the different figures are marked with the same reference numbers.

Figure 1:
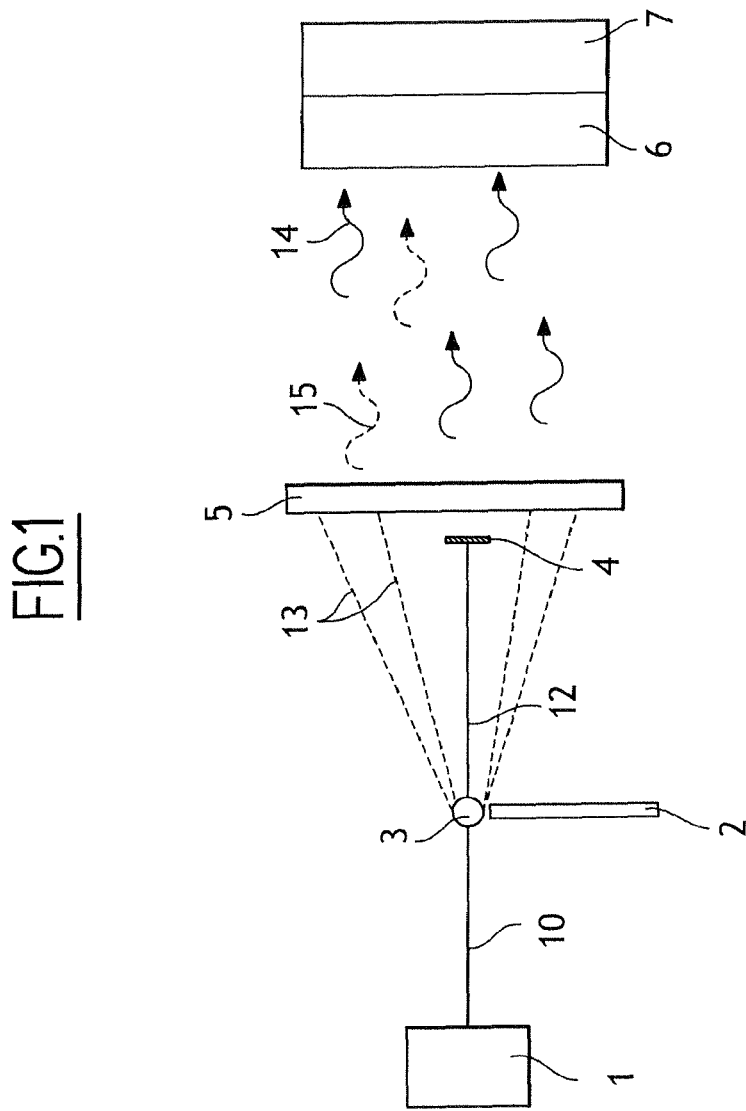
FIG. 1 shows a diagrammatic view of a two-dimensional detection system for neutron radiation according to a first embodiment of the invention.

FIG. 1 shows a diagrammatic view of the two-dimensional detection system for neutron radiation according to a first embodiment of the invention. This detection system comprises an emission means 1, a support means 2 adapted for receiving a sample 3, a filter means 4, a photoemission means 5, an amplification means 6 and a charge-coupled detection device 7.

The detection system according to this invention uses the phenomenon of photoemission produced by some materials activated by neutron radiation. A number of known materials interacts with neutrons to emit usually short-lived radiations. For example, this is the case for helium 3 or lithium 6 that emit alpha radiation, cadmium and gadolinium that emit gamma radiation or boron that emits both alpha and gamma radiations. When inserted in a composite matrix containing photoemitting atoms or molecules, these materials form scintillators that can be activated under the action of a neutron radiation.

These scintillators include two essential categories, namely scintillators involving several different nuclear reactions and that are therefore based on multiple energy transfers, and scintillators involving a single nuclear reaction, and therefore that only involve a single energy transfer. The photoemission means 5 of the detection system is a scintillator of the second category, in other words it only involves a single energy transfer to create photoemission; this photoemission means 5 uses a nuclear reaction that transforms the incident neutrons into alpha radiation. For example, the photoemission means 5 will be a lithium based scintillator and particularly a lithium 6 based scintillator. For neutrons with a wavelength of between 0.5 and 30 Angstroms (Å) for example, the following reaction occurs:

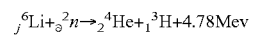

The impact of a neutron on the scintillator converts the lithium into helium (alpha radiation) and tritium, and releases a certain amount of energy. Photoemitting atoms or molecules are charged and transform this energy into light radiation.

Composite materials based on lithium fluoride or lithium sulphide will be used in preference to form the photoemission means 5. A scintillator made of a composite material based on lithium sulphide and with a conversion ratio of $1.5*10^5$ photons per absorbed neutron converts the energy created by neutron radiation into light radiation. The emission wavelength that depends on the doping of the scintillator matrix, is equal to approximately λ=450 nm. Apart from the large quantity of emitted photons per incident neutron, this scintillator is specifically sensitive to neutron radiation because other radiations, such as X or gamma radiation, interact only very slightly with Lithium. Therefore, this provides a means for reducing the parasite effect due to secondary gamma radiation emitted by the environment in contact with neutrons.

The scintillator may be in the form of a plate with dimensions varying from 5 to 100 cm in length and in width and with a thickness less than or equal to 1.2 mm. The small thickness of the scintillator limits absorption of photons in the plate and thus creates greater light radiation. The scintillator is hold in place by a rigid support. The front face of the scintillator is lined with a surface 34 opaque to light and transparent to neutrons. Typically, an aluminium plate with a thickness less than or equal to 1 mm will be used both as the rigid support and the surface 34 opaque to light and transparent to neutrons.

Figure 4:
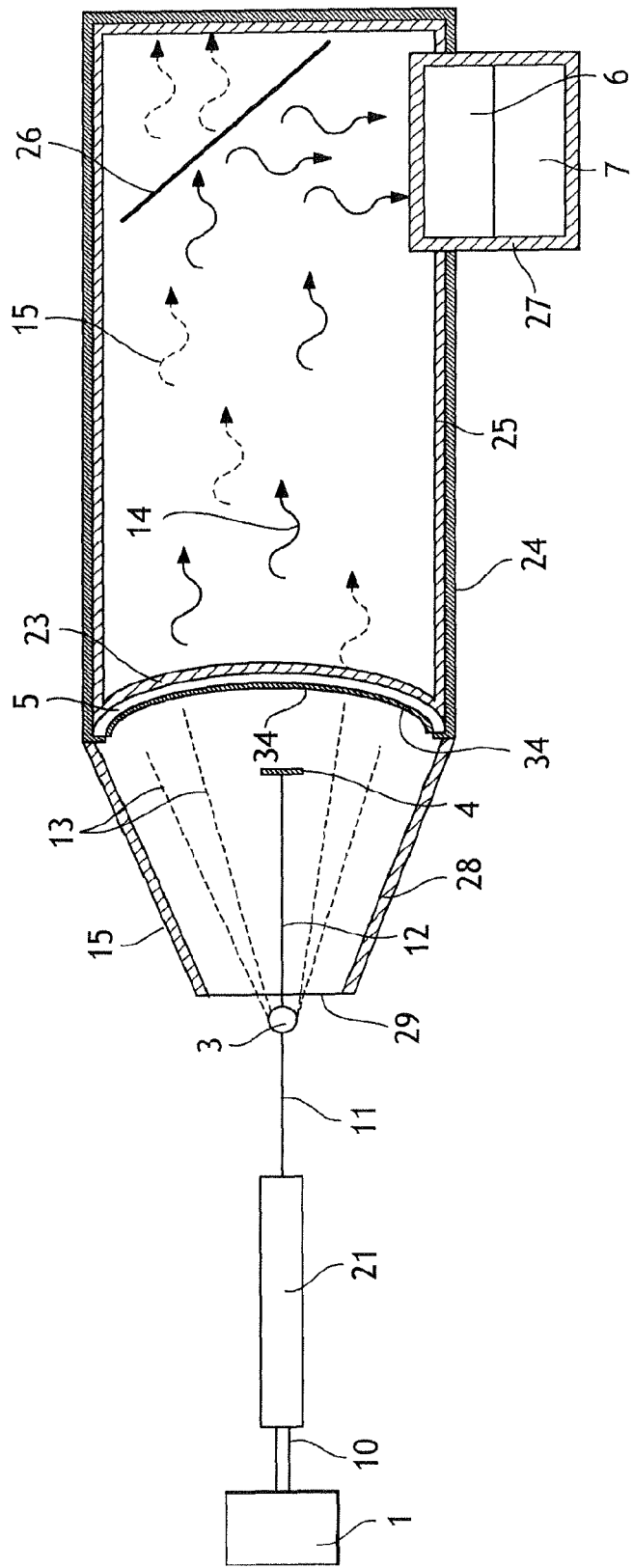
FIG. 4 shows a diagrammatic view of a two-dimensional detection system for neutron radiation according to a fourth embodiment of the invention.

The scintillator in the form of a plate may be plane or curved. A scintillator in the form of a curved plate can be defined by a portion of sphere or cylinder delimited by a rectangular plane with dimensions varying from 5 to 100 cm in length and in width, as shown in FIG. 4. The radius of the sphere or the cylinder is determined as a function of the sample-scintillator distance and of the neutron wavelength, This enables an observation with a constant scattering factor (elastic scattering).

The emission means 1 is configured so as to output a monochromatic neutron beam 10. This monochromatic neutron beam strikes the sample 3 placed on the support means 2. Contact of the monochromatic neutron beam 10 with the sample 3 leads to a scattering characteristic of the organisation of the sample 3.

A filter means 4 is placed between the sample 3 and the photoemission means 5, designed to trap a substantial part of the monochromatic neutron beam transmitted 12 by the sample 3. Indeed, only the monochromatic neutrons beam diffused 13 by the sample 3 enables characterisation of the structural organisation of the sample 3. Therefore, the filter means 4 is adapted for trapping most if not all of the transmitted monochromatic neutron beam 12 such that only the scattered monochromatic neutron beam 13 reaches and activates the scintillator. Furthermore, since the scattered intensity is much lower than the transmitted intensity, the signal corresponding to the transmitted neutrons has a much higher intensity than the signal due to the scattered neutrons. Therefore, trapping the transmitted monochromatic neutron beam 12 provides a means for working with intensities appropriate for the required observation.

The charge-coupled detection device 7 provides a means of quantitatively measuring light radiation emitted by the photoemission means 5. A cooled low light level charge-coupled detection device that uses for example the Pelletier effect (cooling temperatures varying from −10° C. to −45° C.) is used, and which consequently has a low background noise.

An amplification means 6 increases the input light signal to the charge-coupled detection device 7. Thus, the use of a microchannel-plate amplifier provides a means for significantly increasing the intensity of light radiation output from the scintillator. The charge-coupled detection device 7 and the microchannel-plate amplifier can be connected in different ways; this connection may be a simple optical connection or may consist in optical fibres connecting the microchannel-plate amplifier to the pixels of the charge-coupled detection device 7.

It is necessary to be able to observe a large number of light levels simultaneously, so that the measurement made by the charge-coupled detection device 7 can be quantitative. Thus, a charge-coupled detection device 7 coded on at least 12 bits is necessary. An optimum measurement of the diffused signal can be obtained for example by using a charge-coupled detection device 7 coded on 16 bits capable of generating images in an unsigned format (positive integers from 0 to 65536 levels) or a signed format (negative and positive integers varying from −32767 to +32767). Since the range of intensity data to be stored pixel by pixel is large with such a charge-coupled detection device, an appropriate data storage format such as the FIT or FITS (Flexible Image Transport System) format should be chosen.

Further, characterisation of the sample 3 will be better if measurements can be integrated for a determined time. Thus, is used a charge-coupled detection device 7 capable of acquisitions for a variable duration, such as a camera with a variable pause time. Finally, it is useful to use a charge-coupled detection device 7 with a large number of pixels thus being adapted for providing good resolution regardless of the dimensions of the observable surface.

Figure 2:
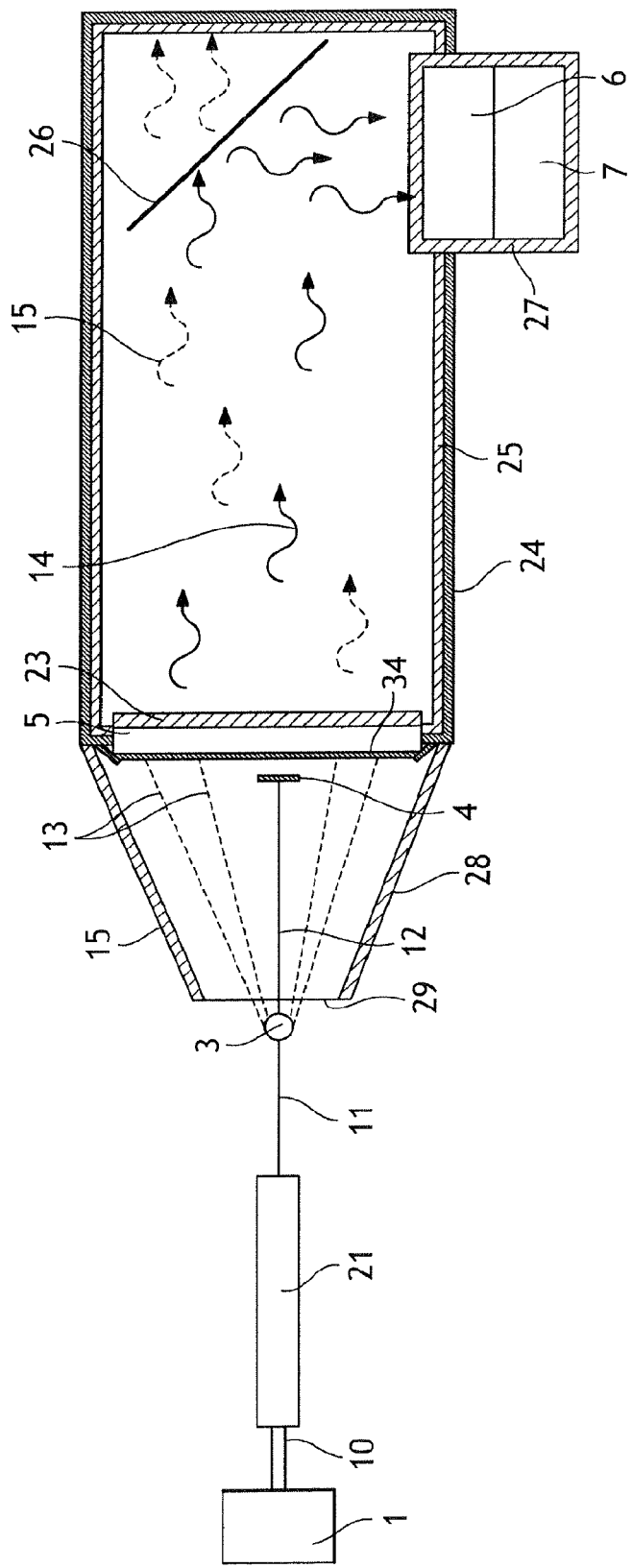
FIG. 2 shows a diagrammatic view of a two-dimensional detection system for neutron radiation according to a second embodiment of the invention.

FIG. 2 shows a diagrammatic view of a two-dimensional detection system for neutron radiation according to a second embodiment of the invention.

The photoemission means 5, the amplification means 6 and the charge-coupled detection device 7 are enclosed in a box 24. More precisely, the photoemission means 5 forms the input wall to the box 24 and the charge-coupled detection device 7 coupled with the amplification means 6 are located at the output end of the box 24. The box 24 is black and is designed so that no other light source than that emitted by the scintillator can penetrate.

The composition of the inside walls 25 of the box 24 is such that neutron and gamma radiation transmitted by the scintillator is absorbed. Thus for example, the inside walls 25 of the box 24 may be covered with boron carbide.

Parasite radiations at the input to the detection system can disturb the measurements, particularly when the sample-scintillator distance becomes greater than 10 cm. A conical or pyramid shaped element 22 can then be provided at the inlet of the box, with the scintillator forming the base of such element. This conical or pyramid shaped element 22 is made so as to reduce the influence of parasite radiation. Thus, this conical or pyramid shaped element 22 comprises sidewalls 28 capable of absorbing parasite radiation not originating from the sample, such as X, neutron or gamma radiation. The conical or pyramid shaped element 22 can also contain an inert gas (such as helium, argon or nitrogen) or a primary vacuum, so as to prevent any interaction between neutrons and ambient air, and particularly absorption and scattering of neutrons by the air or by the moisture contained in the air. The inlet window of the conical or pyramid shaped element 22 comprises a wall 29 transparent to neutrons. Finally, the assembly formed by the box 24 and the conical or pyramid shaped element 22 may be made leak tight.

Figure 3:
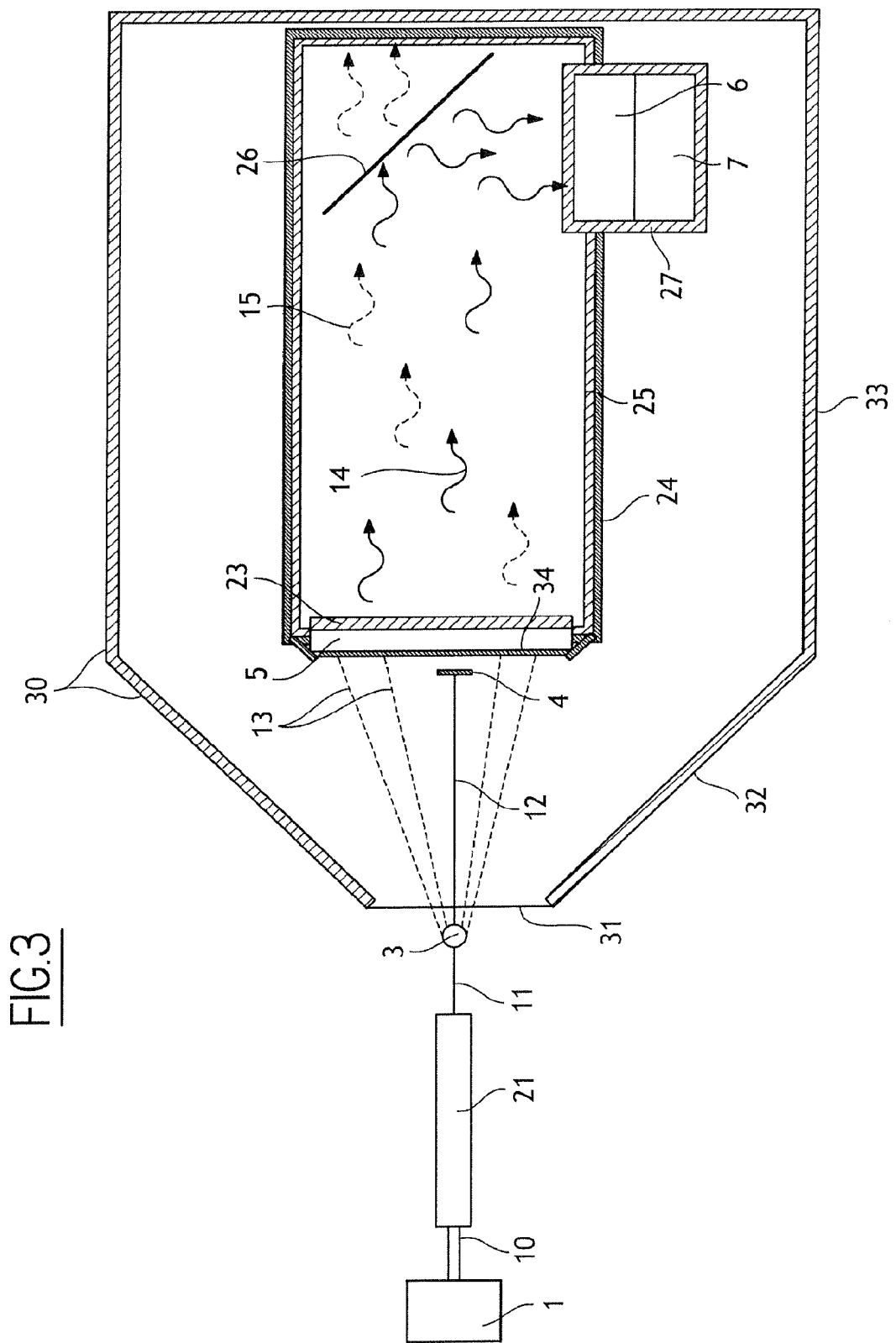
FIG. 3 shows a diagrammatic view of a two-dimensional detection system for neutron radiation according to a third embodiment of the invention.

An alternative means of reducing the influence of parasite radiation is to provide an enclosure 30 like that shown in FIG. 3, comprising a cylindrical part 33 and a tapered end 32. In the same way as the conical or pyramid shaped element 22, the enclosure 30 comprises sidewalls capable of absorbing parasite radiation not originating from the sample, such as X, neutron or gamma radiation. The enclosure 30 may also contain an inert gas such as helium or a primary vacuum, to prevent any interaction between neutrons and ambient air, and particularly absorption and diffusion of neutrons by the air or the moisture contained in the air. The enclosure 30 comprises a wall 31 transparent to neutrons.

The photoemission means 5 that forms the input wall to the box 24 may also be lined on its inside surface by a means 23 of absorbing neutron and gamma radiation. This absorption means 23 may be a boron glass plate, and therefore will be capable of absorbing neutrons that have not been revealed by the scintillator but will also help to reduce gamma radiation, output from the direct beam. A grid marked on the boron glass plate may also be provided to facilitate indexing of the visual field of the charge-coupled detection device 7. The visual field can also be indexed using a reference monocrystalline sample for which the diffusion spectrum is known (for example NaCl (monocrystalline salt), Si (Silicon)).

A shield 27 can be provided around the assembly formed by the charge-coupled detection device 7 and the amplification means 6, to increase the signal/noise ratio of the detection signal. Radiation such as gamma radiation emitted by neutrons transmitted by the scintillator and interacting for example with the air, can namely increase the background noise. Considering a shield defined by its thickness (in cm) and its density, it will then be necessary to provide a shield such that the product of the shield density by its thickness is greater than or equal to 34, to absorb parasite gamma radiation and thus reduce the background noise. For example, a 2 cm thick shield in tungsten (density 18) could be used.

A mirror 26 is placed in the box 24. This mirror 26 may be plane or curved, and is capable of reflecting only light radiation 14 emitted by the photoemission means 5, that is radiation with wavelengths corresponding to the scintillation length of the scintillator, other radiation 15 being therefore transmitted or absorbed but not reflected. As a consequence, the mirror 26 makes an indirect view set up possible, thus eliminating any risk of damage of the charge-coupled detection device 7 by irradiation. This is done by placing the charge-coupled detection device 7 coupled to the amplification means 6 on a sidewall of the box 24 and orienting the mirror 26 at 26° to 45° from the direction of the beam (14,15) output from the photoemission means 5. For a scintillator that emits light radiation in the blue ($\lambda$=450 nm) such as a scintillator made from a composite material based on lithium sulphide, a mirror 26 with a large reflecting capacity in the blue can be chosen such as a thin aluminised quartz mirror, typically less than 10 mm thick.

A collimation device 21 is provided at the output from the emission means 1 and in front of the support means 2 of the sample 3. This collimation device 21 guides and collimates the monochromatic neutron beam 10 output from the emission means 1. Therefore, the diameter of the resultant monochromatic neutron beam 11 will be between 0.5 and 15 mm depending on the set of diaphragms used in the collimation device 21, which will be chosen as a function of the size of the sample to be analysed.

Experience shows that the resolution of measurements depends essentially on the chosen collimation, the intrinsic resolution of the detection system being negligible compared with the influence of collimation on the global resolution. Therefore, the size of the sample that will define the diameter of the monochromatic neutron beam 11 and consequently the parameters of the collimation device such as the length of the collimator, the collimation diaphragms used and the distance between the sample and the scintillator, will have to be taken into account to optimise the global resolution. For example, for small samples, the diameter of the monochromatic neutron beam can be as small as 1 or 2 mm. The result obtained with a sample-scintillator distance of the order of 100 to 150 mm, is a resolution equivalent to that obtained on a conventional detection apparatus of the 2-axis mono detector type with a 10 mm beam and a sample-scintillator distance equal to 1 m. However, the conventional detection apparatus of the 2-axis mono detector type in this configuration with finite dimensions can only cover a small part of the diffusion space, while the detection system according to the invention enables measurement of a much larger part of the diffusion space in a single shot.

We will now present some experimental results obtained with the two-dimensional detection system for neutron radiation according to the invention. Various known samples have been chosen to make test measurements and make comparisons with the performances of conventional spectrometers.

The first diffraction example relates to sapphire monocrystal. Sapphire crystallises into a rhombohedral system (trigonal). This crystal is useful for carrying out tests since a single orientation produces a very wide variety of reflections (sapphire has namely a different distribution of angles for equivalent distances). The sample is a 16 mm diameter and 10 mm thick disk.

Experimental conditions are as follows: collimation output diameter of 12 mm, sample-scintillator distance of 80 mm, pause time of 2.3 seconds, measurements averaged on 80 images.

Figure 5:
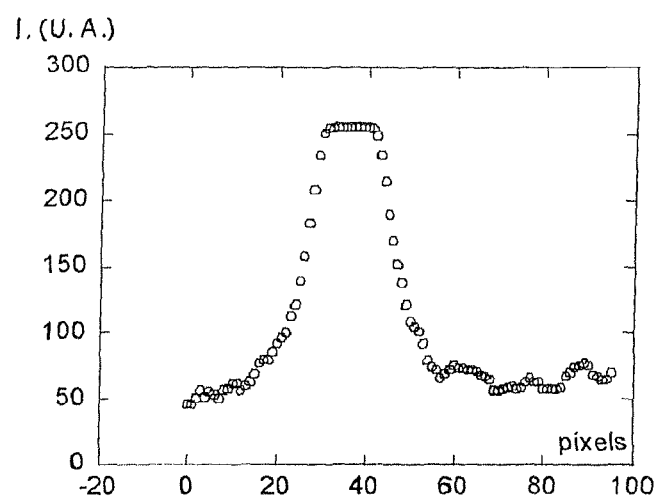
FIG. 5 is a section of a Bragg reflection of the sapphire monocrystal measured with a charge-coupled detection device coded on 8 bits.
Figure 6:
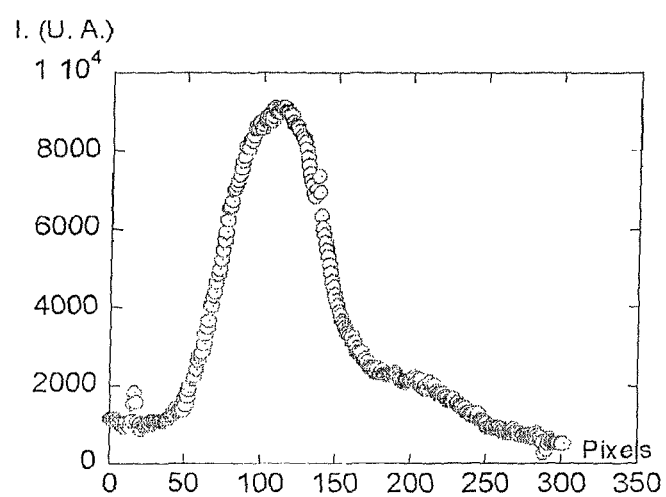
FIG. 6 is a section of a Bragg reflection of the sapphire monocrystal measured with a charge-coupled detection device coded on 16 bits.

FIGS. 5 and 6 are sections of a Bragg reflection of the sapphire crystal measured with charge-coupled detection devices coded on 8 and 16 bits respectively. It is found that the measurement derived from the low level charge-coupled detection device coded on 16 bits is much finer than the measurement derived from the charge-coupled detection device coded on 8 bits, which also demonstrates that the signal is saturated. The precision of the Bragg reflection section in FIG. 6 shows that the detection system according to the invention is genuinely competitive with normal detection techniques.

The second example relates to a liquid crystal. At ambient temperature, it presents a smectic phase characterised by the stack of rod-like liquid crystal molecule layers. The distance separating these layers is about 29 Å. This implies a small angle scattering; therefore the scintillator has to be moved away from the previously chosen position (80 mm). The chosen sample-scintillator distance is 190 mm and the collimation output diameter at the sample is 8 mm.

The sample is a monodomain oriented so that the normal to the smectic layers is horizontal and perpendicular to the incident beam. The cell is in the form of a disk having a 12 mm diameter and being 1 mm thick. FIG. 7 shows two peaks, on each side of the direct beam, separated by 142 pixels (30.5 mm). These peaks correspond to order 001 of the smectic reflection. The corresponding diffusion vector is $Qh=0.21$ Å$^{-1}$, namely a characteristic layer thickness equal to 29.19 Å. The width of the peak at mid-height along the longitudinal axis is estimated to be $\Delta Qh=0.052$ Å$^{-1}$. The width at mid-height in the transverse direction is $\Delta Qk=0.075$ Å$^{-1}$.

The same sample measured on a 3-axis spectrometer with a 20 mm collimation is characterised by equivalent widths at mid-height, namely $\Delta Qh=0.052$ Å$^{-1}$ in the longitudinal direction, and $\Delta Qk=0.125$ Å$^{-1}$ in the transverse direction. X-ray diffusion on a photographic film qualitatively gives an image similar to that obtained with this process. This is not the case on a small angle diffusion spectrometer (DNPA) since the form of the Bragg reflection is then very much modified by the low resolution in wavelength (about 10% in that case).

The reader will have understood that many modifications may be made without departing from the new teachings and advantages described herein. Consequently, all modifications of this type will fall within the scope of the two-dimensional detection system for neutron radiation as defined in the appended claims.

The invention claimed is:

1. Two-dimensional neutron detection system for neutron scattering comprising
   (a) an emission means configured for emitting a monochromatic neutron beam,
   (b) a support means for receiving a sample, arranged in the trajectory of the monochromatic neutron beam;
   (c) a photoemission means for activation by neutrons, arranged in the trajectory of the monochromatic neutron beam after the (b) support means, wherein (c) the photoemission means comprises a lithium-based scintillator which emits alpha radiation originating from a single nuclear reaction;
   (d) a filter means, said filter means being located between (b) the support means and the (c) photoemission means and being adapted for trapping the entire monochromatic neutron beam transmitted by the sample such that scattered neutrons from the sample reach and activate the (c) photoemission means; and
      wherein the (c) photoemission means detects only the number of neutrons scattered by the sample and is in the direct path of the (a) emission means and (d) filter means;
   (e) a cooled low light level charge-coupled detection device,
   (f) an amplification means located upstream of (e) the charge-coupled detection device and coupled with (e) the charge-coupled detection device, said (f) amplification means and said (e) charge-coupled detection device being surrounded by a shield for stopping gamma radiation; and wherein
   said (c) photoemission means, said (f) amplification means, and said (e) charge-coupled detection device are enclosed in a box designed such that no light radiation other than that emitted by the (c) photoemission means can penetrate inside, said (c) photoemission means forming an inlet wall of the box, and said (e) charge-coupled detection device coupled with said (f) amplification forming an outlet wall of the box, wherein the outlet wall is adjacent to the inlet wall.

2. Two-dimensional neutron detection system for neutron scattering according to claim 1, wherein the lithium-based scintillator is a composite material based on lithium sulphide.

3. Two-dimensional neutron detection system for neutron scattering according to claim 1, wherein the lithium-based scintillator is a composite material based on lithium fluoride.

4. Two-dimensional neutron detection system for neutron scattering according to claim 1,
   wherein
   (c) the photoemission means is in the form of a plate with a length of between 5 and 100 cm, a width of between 5 and 100 cm and a thickness of less than or equal to 1.2 mm.

5. Two-dimensional neutron detection system for neutron scattering according to claim 1, wherein (c) the photoemission means is plane.

6. Two-dimensional neutron detection system for neutron scattering according to claim 1, wherein (c) the photoemission means is curved, defined by a portion of cylinder delimited by a plane with dimensions varying from 5 to 100 cm in length and in width.

7. Two-dimensional neutron detection system for neutron scattering according to claim 1, wherein (c) the photoemission means is curved, defined by a portion of sphere.

8. Two-dimensional neutron detection system for neutron scattering according to claim 1, wherein (c) the photoemission means is lined with a surface opaque to light and transparent to neutron scattering, and located on the inlet of (c) the photoemission means.

9. Two-dimensional neutron detection system for neutron scattering according to claim 8, wherein the opaque surface is formed from a rigid material adapted for holding (c) the photoemission means in place.

10. Two-dimensional neutron detection system for neutron scattering according to claim 8, wherein the opaque surface is an aluminum plate.

11. Two-dimensional neutron detection system for neutron scattering according to claim 1, wherein (e) the charge-coupled detection device enables coding on at least 12 bits.

12. Two-dimensional neutron detection system for neutron scattering according to claim 11, wherein (e) the charge-coupled detection device enables coding on at least 16 bits.

13. Two-dimensional neutron detection system for neutron scattering according to claim 1, wherein (e) the charge-coupled detection device is a camera adapted for variable pause times.

14. Two-dimensional neutron detection system for neutron scattering according to claim 1,
   wherein
   the system further comprises a protection means capable of reducing the influence of parasite radiation between the (b) support means for the sample and (c) the photoemission means.

15. Two-dimensional neutron detection system for neutron scattering according to claim 14, wherein the protection means is a conical or pyramid shaped element, having (c) the photoemission means as its base and being located between (b) the support means for the sample and (c) the photoemission means.

16. Two-dimensional neutron detection system for neutron scattering according to claim 14, wherein the protection means is a casing comprising a cylindrical part and a tapered end part, and surrounding the box.

17. Two-dimensional neutron detection system for neutron scattering according to claim 14, wherein the protection means includes sidewalls adapted for absorbing parasite radiation not originating from the sample.

18. Two-dimensional neutron detection system for neutron scattering according to claim 14, wherein the protection means contains an inert gas or a primary vacuum.

19. Two-dimensional neutron detection system for neutron scattering according to claim 18, wherein the inert gas is helium.

20. Two-dimensional neutron detection system for neutron scattering according to claim 18, wherein the inert gas is argon.

21. Two-dimensional neutron detection system for neutron scattering according to claim 18, wherein the inert gas is nitrogen.

22. Two-dimensional neutron detection system for neutron scattering according to claim 1, wherein the box comprises inside walls adapted for absorbing neutron and gamma radiation.

23. Two-dimensional neutron detection system for neutron scattering according to claim 1, wherein the system further comprises a minor adapted for reflecting only light radiation emitted by (c) the photoemission means towards (f) the amplification means.

24. Two-dimensional neutron detection system for neutron scattering according to claim 23, wherein the minor is made from aluminized quartz and is less than or equal to 10 mm thick.

25. Two-dimensional neutron detection system for neutron scattering according to claim 23, wherein the minor is plane.

26. Two-dimensional neutron detection system for neutron scattering according to claim 23, wherein the minor is curved.

27. Two-dimensional neutron detection system for neutron scattering according to claim 1, wherein the system further comprises a means for absorbing neutron and gamma radiation, this absorption means being arranged at the outlet of (c) the photoemission means.

28. Two-dimensional neutron detection system for neutron scattering according to claim 1, wherein the shield is a metal with a thickness and a density such that the product of the thickness and the density is greater than or equal to 34.

29. Two-dimensional neutron detection system for neutron scattering according to claim 1, wherein the shield is made of tungsten with a thickness of about 2 cm.

30. Two-dimensional neutron detection system for neutron scattering according to claim 1, wherein the system further comprises a collimation device arranged between (a) the emission means and (b) the support means, and outputting an output neutron beam with a diameter of between 0.5 and 15 mm.

31. Two-dimensional neutron detection system for neutron scattering according to claim 1 wherein (c) the photoemission means device detects only the number of neutrons scattered by a sample at wide diffusion angles.

32. Two-dimensional neutron detection system for neutron scattering according to claim 1, wherein said two-dimensional neutron detection system consists essentially of:
(a) an emission means configured for emitting a monochromatic neutron beam,
(b) a support means for receiving a sample, arranged in the trajectory of the monochromatic neutron beam;
(c) a photoemission means for activation by neutrons, arranged in the trajectory of the monochromatic neutron beam after the (b) support means, wherein (c) the photoemission means comprises a lithium-based scintillator which emits alpha radiation originating from a single nuclear reaction;
(d) a filter means, said filter means being located between (b) the support means and the (c) photoemission means and being adapted for trapping the entire monochromatic neutron beam transmitted by the sample such that scattered neutrons from the sample reach and activate the (c) photoemission means; and
wherein the (c) photoemission means detects only the number of neutrons scattered by the sample and is in the direct path of the (a) emission means and (d) filter means;
(e) a cooled low light level charge-coupled detection device,
(f) an amplification means located upstream of (e) the charge-coupled detection device and coupled with (e) the charge-coupled detection device, said (f) amplification means and said (e) charge-coupled detection device being surrounded by a shield for stopping gamma radiation; and wherein
said (c) photoemission means, said (f) amplification means, and said (e) charge-coupled detection device are enclosed in a box designed such that no light radiation other than that emitted by the (c) photoemission means can penetrate inside, said (c) photoemission means forming an inlet wall of the box, and said (e) charge-coupled detection device coupled with said (f) amplification forming an outlet wall of the box, wherein the outlet wall is adjacent to the inlet wall.

* * * * *